US008830297B2

(12) United States Patent
Kim et al.

(10) Patent No.: US 8,830,297 B2
(45) Date of Patent: Sep. 9, 2014

(54) APPARATUS AND METHOD FOR PROVIDING REMOTE MEDICAL SERVICES VIA AN API AND AN OPEN IPTV PLATFORM APPARATUS

(75) Inventors: Eung-Ha Kim, Daejeon-si (KR); Sun-Joong Kim, Daejeon-si (KR); Won-Joo Park, Daejeon-si (KR); Kee-Seong Cho, Daejeon-si (KR); Won Ryu, Daejeon-si (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 329 days.

(21) Appl. No.: 12/877,424

(22) Filed: Sep. 8, 2010

(65) Prior Publication Data
US 2011/0154419 A1    Jun. 23, 2011

(30) Foreign Application Priority Data
Dec. 18, 2009   (KR) .................. 10-2009-0127287

(51) Int. Cl.
| H04N 7/14 | (2006.01) |
| H04N 7/173 | (2011.01) |
| H04N 5/445 | (2011.01) |
| H04N 7/15 | (2006.01) |
| H04L 12/28 | (2006.01) |
| H04N 21/4722 | (2011.01) |
| H04N 7/18 | (2006.01) |
| G06F 3/048 | (2013.01) |
| G06F 15/173 | (2006.01) |
| G06F 15/16 | (2006.01) |
| G06F 3/00 | (2006.01) |
| H04N 21/462 | (2011.01) |
| G06F 9/44 | (2006.01) |
| H04L 29/08 | (2006.01) |
| G06Q 10/10 | (2012.01) |
| G06F 9/54 | (2006.01) |

(52) U.S. Cl.
CPC .............. *H04N 7/15* (2013.01); *H04N 7/147* (2013.01); *H04N 7/142* (2013.01); *H04N 7/181* (2013.01); *H04L 12/2801* (2013.01); *H04N 7/17309* (2013.01); *H04N 21/4722* (2013.01); *H04N 7/152* (2013.01); *H04N 21/4622* (2013.01); *H04N 7/17318* (2013.01); *G06F 8/34* (2013.01); *G06F 3/0841* (2013.01); *H04L 29/08072* (2013.01); *G06Q 10/10* (2013.01); *G06F 9/541* (2013.01); *Y10S 715/97* (2013.01)
USPC .................. 348/14.1; 348/14.03; 348/14.04; 348/14.07; 348/143; 725/106; 725/117; 725/61; 725/51; 725/110; 715/771; 715/970; 709/224; 709/205; 709/218; 719/328

(58) Field of Classification Search
CPC ......... H04N 7/15; H04N 7/147; H04N 7/142; H04N 7/152; H04N 7/181; H04N 7/17309; H04N 21/4622; H04N 21/4722; H04N 7/17318; H04L 12/2801; H04L 29/08072; G06F 8/34; G06F 3/0481; G06F 9/541; G06Q 10/10
USPC ........... 725/106, 117, 110, 61, 51; 348/14.03, 348/14.04, 14.07, 14.1, 143; 715/771, 970; 709/224, 205, 218; 719/328
See application file for complete search history.

(56) References Cited

U.S. PATENT DOCUMENTS

| 6,454,708 B1 * | 9/2002 | Ferguson et al. ............. 600/300 |
| 2006/0195564 A1 | 8/2006 | Accardi et al. |
| 2006/0205564 A1 | 9/2006 | Peterson |
| 2007/0162304 A1 * | 7/2007 | Rodgers ............................ 705/2 |
| 2007/0219059 A1 * | 9/2007 | Schwartz et al. ................. 482/8 |

FOREIGN PATENT DOCUMENTS

| KR | 10-2002-0015621 | 2/2002 |
| KR | 10-2009-0116849 | 11/2009 |

OTHER PUBLICATIONS

Jin-Ok Jeon, IPTV-based Healthcare Contents Delivery Services, Jun. 20, 2008.*

Kim Ji Yeon, "KT provides IPTV health information service called 'Dream Care TV'", in partnership with BIT Computer Co., Ltd., Oct. 6, 2009.

* cited by examiner

*Primary Examiner* — Hoang-Vu A Nguyen-Ba
(74) *Attorney, Agent, or Firm* — Staas & Halsey LLP

(57) ABSTRACT

An Open Internet Protocol Television (IPTV) platform is provided. By providing remote medical services to users in the Open IPTV environment using a remote medical service providing apparatus including: an application programming interface (API) calling unit to call, when receiving a request for receiving a remote medical service from a counselor's terminal, an API of an Open Internet Protocol Television (IPTV) platform; and a service provider to provide the remote medical service to a user through the API, it is possible to provide remote medical service operators with environments where they can develop and share various remote medical to services and content.

17 Claims, 5 Drawing Sheets

APPARATUS AND METHOD FOR PROVIDING REMOTE MEDICAL SERVICES VIA AN API AND AN OPEN IPTV PLATFORM APPARATUS

CROSS-REFERENCE TO RELATED APPLICATION

This application claims the benefit under 35 U.S.C. §119(a) of a Korean Patent Application No. 10-2009-0127287, filed on Dec. 18, 2009, the entire disclosure of which is incorporated herein by reference for all purposes.

BACKGROUND

1. Field

The following description relates to an Open Internet Protocol Television (IPTV) platform, and more particularly, to a technique for providing various application services in an Open IPTV platform environment.

2. Description of the Related Art

In general, Internet Protocol Television (IPTV) technology provides broadcasting services, Video on Demand (VoD) services and interactive television services over the wired Internet by combining communication technology with broadcasting technology. The IPTV technology is evolving to accommodate various content and applications on the Internet using open interfaces.

Recently, concerns on a remote medical service for providing medical information and medical services to users living at remote sites are increasing. The remote medical service provides medical information and doctors' professional advice to users living a long distance away. The remote medical service is a comprehensive concept including medical treatment, medical administration, medical education, video telephony between doctors and patients, etc., which are carried out at a remote site.

An example of such remote medical treatment is to allow a user to transmit his or her blood pressure or glucose level from home to a medical institution through the Internet or a cable TV network and receive the results of medical examinations from the medical institution.

SUMMARY

The following description relates to a technique for providing various remote medical services in an Open Internet Protocol Television (IPTV) environment.

In one general aspect, there is provided a remote medical service providing apparatus including: an application programming interface (API) calling unit to call, when receiving a request for receiving a remote medical service from a counselor's terminal, an API of an Open Internet Protocol Television (IPTV) platform; and a service provider to provide the remote medical service to a user through the API.

Therefore, remote medical services are provided in the Open IPTV platform environment, thereby providing remote medical service operators with environments where they can develop and share various remote medical services and content. Accordingly, limitations of existing remote medical services and existing content development environments may be overcome.

Also, since an IPTV, which is a user-friendly interface, is used when a remote medical service user consults with a counselor in real time, the utilization range of service interfaces may extend.

In addition, the utilization scheme of remote medical-related application programming interfaces (APIs) and enablers that have already been built or will be built in the future is proposed to reduce costs for development of new remote medical services that can be proposed as new business models.

Other features and aspects will be apparent from the following detailed description, the drawings, and the claims.

Figure 1:
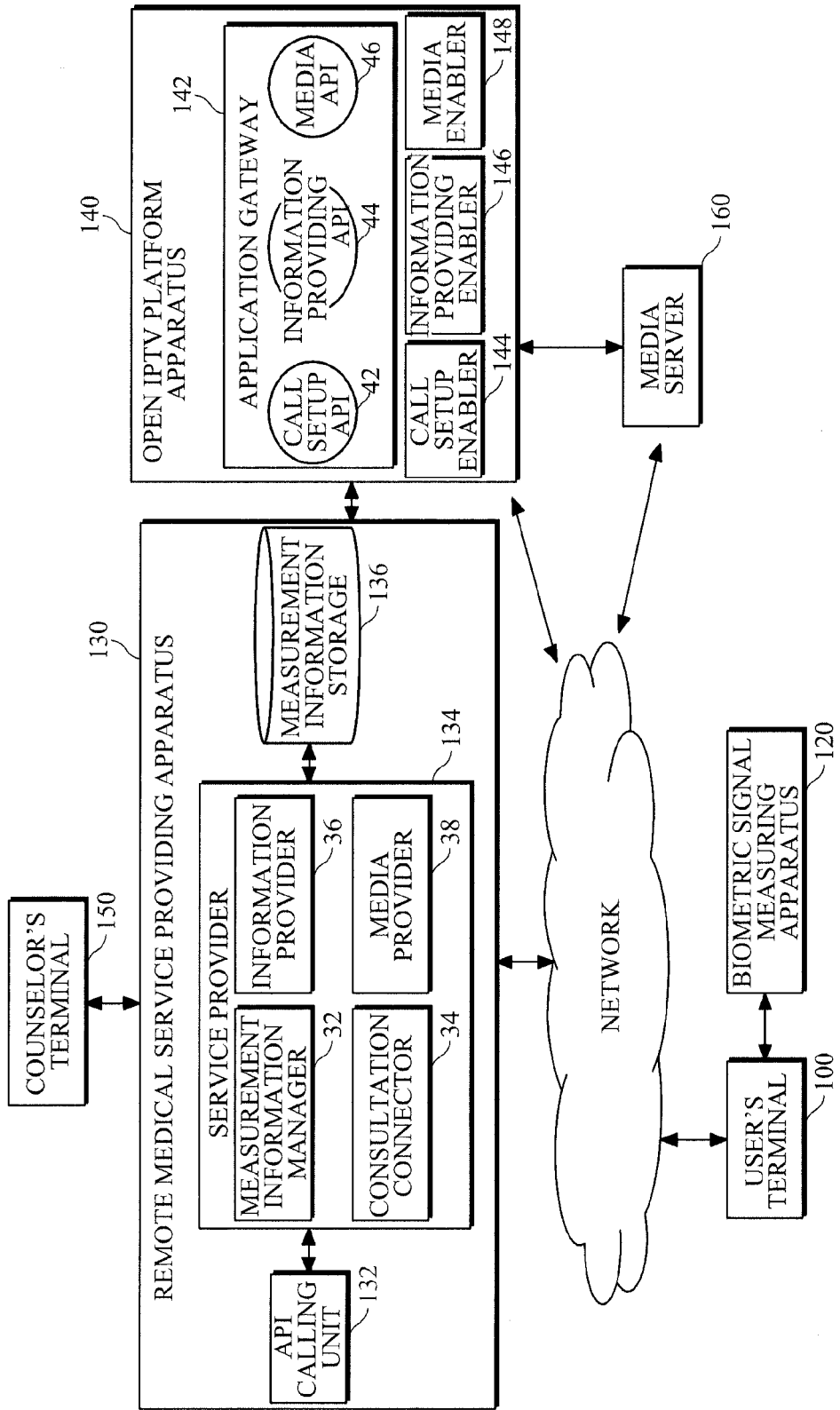
FIG. 1 is a diagram illustrating an example of a remote medical service providing system.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. Also, descriptions of well-known functions and constructions may be omitted for increased clarity and conciseness.

FIG. 1 is a diagram illustrating an example of a remote medical service providing system.

Referring to FIG. 1, the remote medical service providing system includes a user's terminal 100, a counselor's terminal 150, a biometric signal measuring apparatus 120, a remote medical service providing apparatus 130, an Open Internet Protocol Television (IPTV) platform apparatus 140 and a media server 160.

The user's terminal 100 may be an IPTV setup box. The biometric signal measuring apparatus 120 measures a user's biometric signals and transmits the results of the measurement to the user's terminal 100. The biometric signal measuring apparatus 120 includes technical configurations, such as body weight scales, a sphygmomanometer, or the like, to measure height, to weight, blood pressure or heart rate.

Also, the counselor's terminal 150 may be a wired or wireless telephone or a terminal having video telephony functionality. The media server 160 may be a video on demand (VoD) providing apparatus. According to an example, the media server 160 stores exercise video data. The media server 160 extracts corresponding exercise video data in response to a service call from the Open IPTV platform apparatus 140 and transmits the exercise video data to the Open IPTV platform apparatus 140.

A service user measures his or her biometric information, such as a weight, blood pressure or the like, using the biometric signal measuring apparatus 120, and transmits the measurement data to the remote medical service providing apparatus 130.

The remote medical service providing apparatus 130 compares the measurement data with a pre-stored reference value and analyzes the result of the comparison. Then, when the result of the analysis indicates that the measurement data is within a normal range, the remote medical service providing apparatus 130 transmits a message informing of a normal status to the user's terminal 100. On the other hand, if the result of the analysis indicates that the measurement data is not within the normal range, the remote medical service providing apparatus 130 calls the counselor's terminal 150.

The counselor selects a counseling service menu through the counselor's terminal 150 and the remote medical service providing apparatus 130 calls a counseling Application Programming Interface (API) of the Open IPTV platform apparatus 140.

Then, when the counselor requests the remote medical service providing apparatus 130 to send the measurement data of the service user with whom the counselor is in consultation, the remote medical service providing apparatus 130 calls an information providing API of the Open IPTV platform apparatus 140. Then, the Open IPTV platform apparatus 140 activates an information providing enabler 146 to operate the information providing API, thus providing a consultation environment where both the counselor and service user can see the measurement data.

In addition, when the counselor requests the remote medical service providing apparatus 130 to recommend an exercise VoD for the service user with whom the counselor is in consultation, the remote medical service providing apparatus 130 calls a media API of the Open IPTV platform apparatus 140. At this time, the Open IPTV platform apparatus 140 activates a media enabler 148 to operate an API for exercise-related VoD The counselor may select an exercise suitable for treatment of the service user and explain the exercise while viewing an exercise media simultaneously with the service user.

In detail, the remote medical service providing apparatus 130 includes an API calling unit 132, a service provider 134 and a measurement information storage 136.

The API calling unit 132 calls a corresponding API of an application gate 142 which is provided by the Open IPTV platform apparatus 140, according to a service type activated by the service provider 134.

The measurement information storage 136 stores measurement information on the user's biometric signal, which is received from the user's terminal 100 and has been measured by the biometric signal measuring apparatus 120.

The service provider 134 includes a measurement information manager 32, a consultation connector 34, an information provider 36 and a media provider 38.

The measurement information manager 32 receives measurement information on a user's biometric signal that has been measured by the biometric signal measuring apparatus 120, from the user's terminal 100. The user measures his or her weight, blood pressure or the like using the biometric signal measuring apparatus 120 and transmits the measurement data to the remote medical service providing apparatus 130 through the user's terminal 100. The measurement information manager 32 databases the measurement data on the user's biometric signal, stores it in the measurement information storage 136 and then manages it.

Then, the measurement information manager 32 compares the measurement data with a reference value and analyzes the result of the comparison. If the result of the analysis indicates that the measurement data is within a normal range, the measurement information manager 32 transmits a message informing of a normal status to the user's terminal 100. The user checks that his or her heath is at a normal status through the user's terminal and may request the remote medical service providing apparatus 130 to provide a remote medical service.

Meanwhile, if the measurement information manager 32 determines that the measurement data is not within the normal range, the consultation connector 34 automatically calls the counselor's terminal 150. For example, the consultation connector 34 provides information about the user whose measurement data is not within the normal range. Then, when the counselor selects a call setup menu to consult with the user whose measurement data is not within the normal range, the consultation connector 34 calls a call setup API function that is provided by the Open IPTV platform apparatus 140 in order to provide a consultation service.

When receiving a shared view service request from the counselor's terminal 150, the information provider 36 calls the information providing API 44 corresponding to the shared view service in the Open IPTV platform apparatus 140, wherein the shared view service means providing a certain service or data to two or more terminals at the same time in order for users of the terminals to view the service or data at the same time.

When receiving an exercise media service request from the counselor's terminal 150, the media provider 38 calls the media API 46 of the Open IPTV platform apparatus 140.

Also, the Open IPTV platform apparatus 140 includes the application gateway 142 to provide APIs and enablers.

In order to operate the call setup API 42 called by the consultation connector 34 of the remote medical service providing apparatus 130, the application gateway 142 activates a call setup enabler 144 associated with the call setup API 42 to perform a call setup for consultation.

The call enabler 144 which has received the call setup request connects sessions to both the counselor's terminal 150 and user's terminal 100, thereby performing a call setup to allow video telephony between the counselor's terminal 150 and the user's terminal 100.

In order to operate the information providing API 44, execution of the shared view service for measurement data of biometric signals is required to the information providing enabler 146 associated with the information providing API 44.

Then, the information providing enabler 146 extracts measurement data on the user from the measurement information storage 136 of the remote medical service providing apparatus 130, and transmits the measurement information simultaneously to both the counselor's terminal 150 and user's terminal 100. Then, the counselor's terminal 150 and user's terminal 100 display the measurement data about the user through viewers, so that the counselor and user can simultaneously examine the measurement data while talking over the telephone.

When the counselor requests another kind of measurement data, the information providing enabler 146 extracts the requested kind of measurement data from the measurement information storage of the remote medical service providing apparatus 130 and transmits the extracted data to both the counselor's terminal 150 and the user's terminal 100.

Then, in order to operate the media API 46, the media enabler 148 for providing an exercise VoD service is activated.

The media enabler 148 transmits information on exercise VoD content requested by the Jo counselor to the media server 160 which stores exercise VoD. The media server 160 detects a location at which the corresponding exercise VoD content is stored and transmits the location information of the exercise VoD content to the media enabler 148. Then, the media enabler 148 transmits the received location information of the exercise VoD content to both the counselor's terminal 150 and user's terminal 100.

Successively, the counselor's terminal 150 and user's terminal 100 access the media server 160 based on the location information of the exercise VoD media content, to request the media server 160 to send exercise VoD streams or to receive the exercise VoD content from the media server 160.

Also, when the counselor additionally selects other exercise VoD content, the media enabler 148 may transmit information on a location at which the additionally requested exercise VoD content is stored to both the counselor's terminal 150 and user's terminal 100, so that the counselor's terminal 150 and user's terminal 100 can simultaneously display the additionally requested exercise VoD content.

Figure 2:
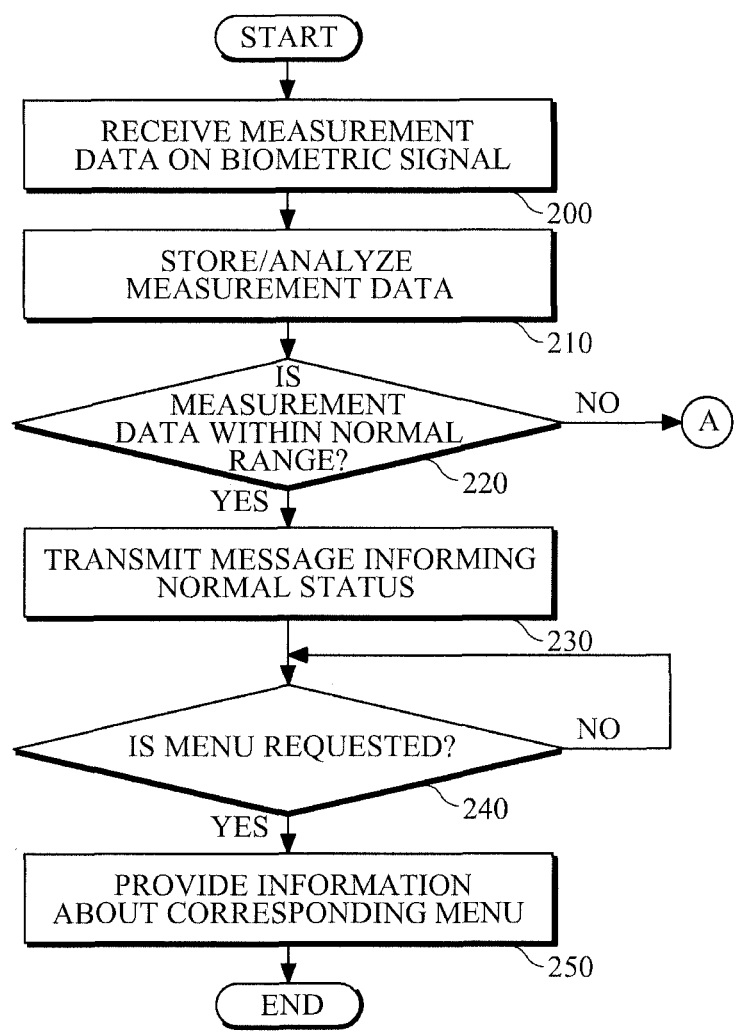
FIG. 2 is a flowchart illustrating an example of a method of managing measurement data and receiving a service request.
Figure 3:
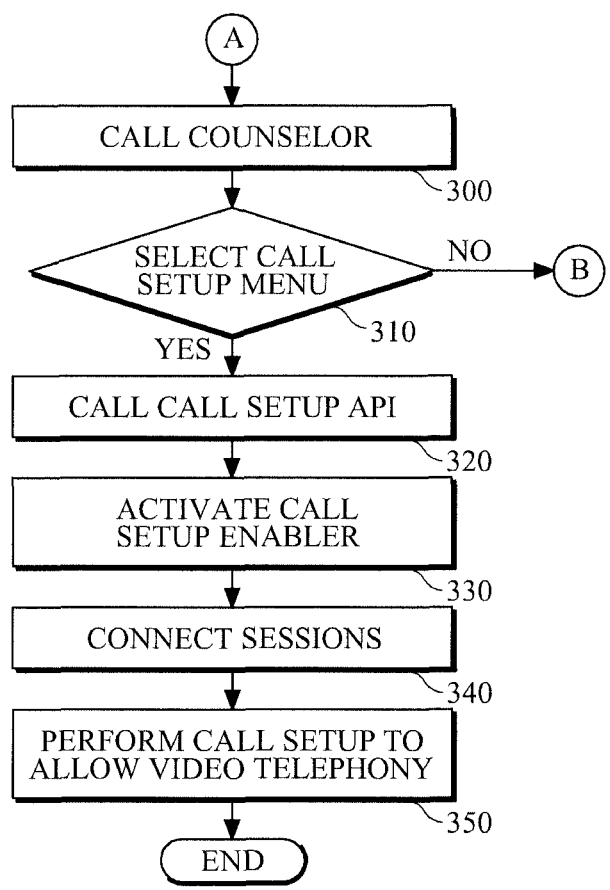
FIG. 3 is a flowchart illustrating an example of a call setup method.
Figure 4:
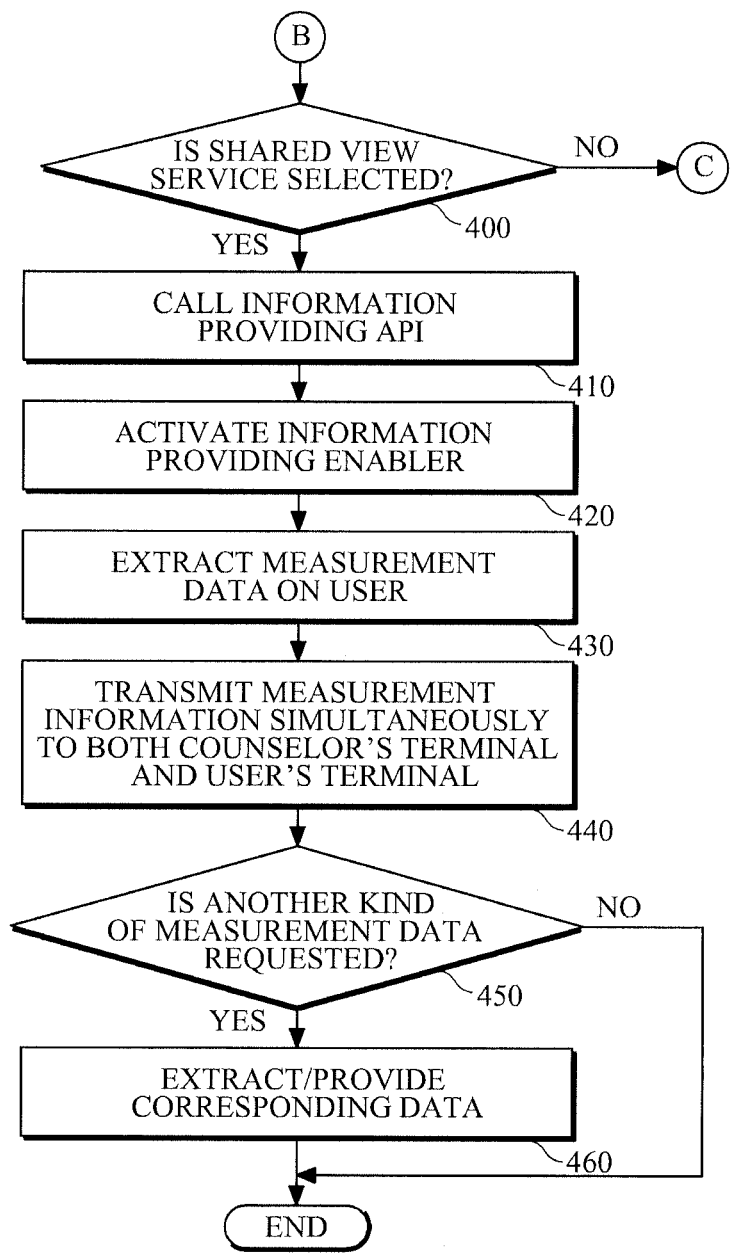
FIG. 4 is a flowchart illustrating an example of a method of providing measurement information on a biometric signal.
Figure 5:
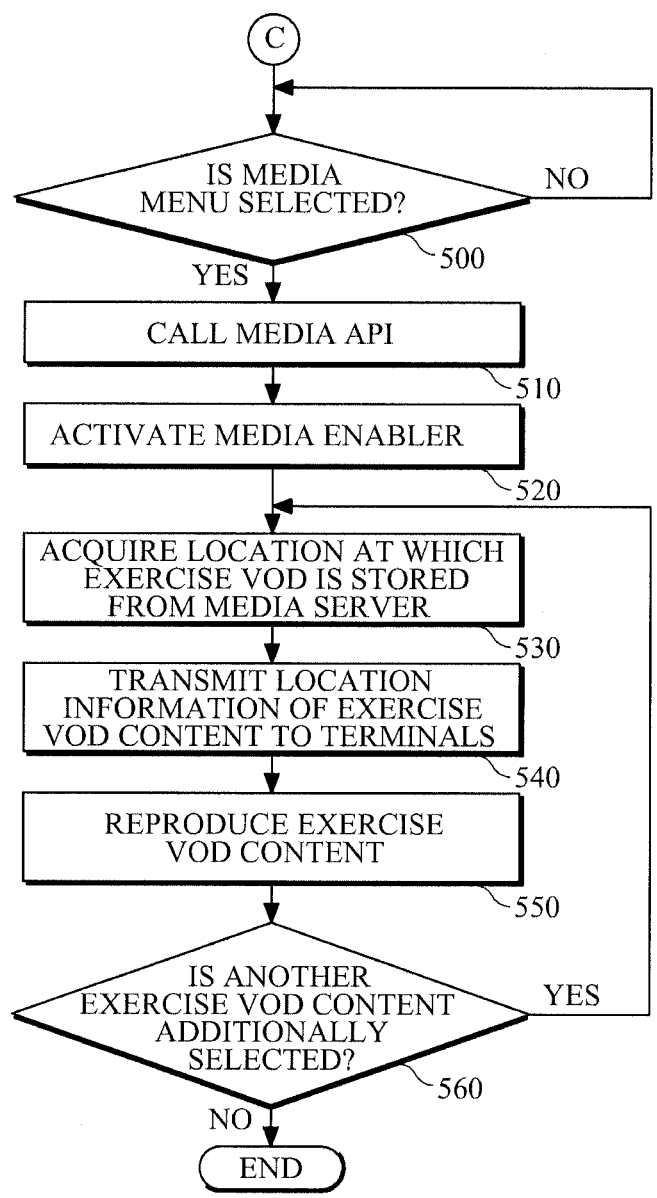
FIG. 5 is a flowchart illustrating an example of a media providing method.

FIGS. 2 to 5 are flowcharts illustrating an example of a remote medical service providing method, wherein FIG. 2 is a flowchart illustrating an example of a method of managing measurement data and receiving a service request, FIG. 3 is a flowchart illustrating an example of a call setup method, FIG. 4 is a flowchart illustrating an example of a method of providing measurement information on a biometric signal, and FIG. 5 is a flowchart illustrating an example of a media providing method.

First, referring to FIG. 2, a user measures his or her biometric signal, such as weight, blood pressure or the like. The measurement data of the user's biometric signal is transmitted to a remote medical service providing apparatus. In other words, the remote medical service providing apparatus receives measurement data of a user's biometric signal from a user's terminal (operation 200).

The remote medical service providing apparatus databases, stores and manages measurement data of subscribers' biometric signals. The remote medical service providing apparatus compares the measurement data with a reference value (operation 210).

Successively, it is determined whether the measurement data is within a normal range based on the result of the comparison (operation 220). When it is determined that the measurement data is within the normal range, the remote medical service providing apparatus transmits a message informing of a normal status to the user's terminal (operation 230).

Accordingly, the user may check his or her health status through the user's terminal and request remote medical service according to the checked result (operation 240). When the user requests remote medical service, the remote medical service providing apparatus may transmit user menu information to the user's terminal which is, for example, an IPTV set-top box. The user menu is configured in a form to allow a user to select a desired remote medical service and select analysis data on at least one piece of his or her biometric data. The user may select at least one information item, such as blood pressure and body fat, from the user menu, and the remote medical service providing apparatus provides information corresponding to the information item selected by the user to the user's terminal (operation 250).

Meanwhile, when the measurement data is not within the normal range, referring to FIG. 3, the remote medical service providing apparatus automatically calls a counselor's terminal (operation 300). If the counselor selects a call setup menu to consult with the user (operation 310), the remote medical service providing apparatus calls a call setup API provided by an Open IPTV platform apparatus in order to provide a consultation service (operation 320). In order to execute the call setup API, an application gateway in the Open IPTV platform apparatus activates a call setup enabler associated with the call setup API and requests the call setup enabler to perform a call setup for consultation (operation 330).

The call setup enabler that has received the call setup request connects sessions to both the counselor's terminal and user's terminal (operation 340), thereby performing a call setup to allow video telephony between the counselor's terminal and the user's terminal (operation 350).

The counselor monitors the user's measurement data through a menu that is provided by the remote medical service providing apparatus to select a counseling service item. Referring to FIG. 4, the counselor may select a shared view service as necessary while talking with the user over the telephone in order to explain the user's measurement data (operation 400). When receiving a shared view service request from the counselor's terminal, the remote medical service providing apparatus calls an information providing API corresponding to the shared view service in the Open IPTV platform apparatus (operation 410). The application gateway of the Open IPTV platform apparatus requests, in order to operate the information providing API, an information providing enabler associated with the information providing API to execute the shared view service (operation 420).

The information providing enabler extracts the user's measurement data from measurement information storage of the remote medical service providing apparatus (operation 430) and then transmits the extracted measurement data to both the counselor's terminal and user's terminal (operation 440). The counselor's terminal and user's terminal display the user's measurement data through viewers. Accordingly, the counselor and user can simultaneously examine the measurement data on the user while talking over the telephone.

Thereafter, when the counselor requests another kind of measurement data (operation 450), the information providing enabler extracts the corresponding kind of measurement data from the measurement data storage of the remote medical service providing apparatus, and transmits the extracted data to both the counselor's terminal and user's terminal (operation 460).

Thereafter, when the counselor recommends an exercise needed for the user based on the user's measurement data, the counselor may select an exercise media service through the counselor's terminal. The exercise media service is used to more efficiently provide medical consultation by providing a media file relating to an exercise needed for a user based on measurement information on the user's biometric signal.

Referring to FIG. 5, when receiving an exercise media service request (operation 500), the remote medical service providing apparatus calls a media API of the Open IPTV platform apparatus (operation 510). Then, in order to execute the called media API, the remote medical service providing apparatus activates a media enabler for providing an exercise VoD service (operation 520).

Then, the media enabler transmits information on exercise VoD content requested by the counselor to the media server which stores exercise VoD. The media server detects a location at which the corresponding exercise VoD content is stored and transmits the location information to the media enabler (operation 530). The media enabler transmits the location information of the exercise VoD content to both the counselor's terminal and user's terminal (operation 540).

The counselor's terminal and user's terminal access the media server based on the location information of the exercise VoD media content, to request the media server to send exercise VoD streams or to receive the exercise VoD content from the media server.

Accordingly, the counselor may explain an efficient exercise method to the user while viewing exercise VoD content suitable for the user simultaneously with the user (operation 550).

Also, when the counselor additionally selects other exercise VoD content (operation 560), the media enabler may transmit information on a location at which the additionally requested exercise VoD content is stored to both the counselor's terminal and user's terminal, so that the counselor's terminal and user's terminal simultaneously display the additionally requested exercise VoD content (operations 530, 540 and 550).

Meanwhile, the remote medical service providing method described above may be recorded as a computer program. The program may be stored in a computer-readable recording medium and implemented by being read and executed by a computer. The computer-readable recording medium may include a magnetic recording medium, an optical recording medium, or the like.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A remote medical service providing apparatus comprising:
   an application programming interface (API) calling unit, executed by a processor, to call, when receiving a request for receiving a remote medical service from a counselor's terminal, a call setup API, an information providing API, and a media API of an Open Internet Protocol Television (IPTV) platform, such that the calling of the APIs is performed according to the request received from the counselor's terminal; and
   a service provider to provide the remote medical service to a user through the API using video telephony, when the call setup API is called,
   wherein each of the call setup API, the information providing API, and the media API corresponds to a different application service than the other APIs.

2. The remote medical service providing apparatus of claim 1, further comprising a measurement information storage to store measurement information on the user's biometric signal,
   wherein the service provider comprises a measurement information manager to receive the measurement information on the user's biometric signal from the user's terminal and store the measurement information on the user's biometric signal in the measurement information storage.

3. The remote medical service providing apparatus of claim 2, wherein the service provider comprises an information provider to call, when receiving a request for receiving information from the counselor's terminal, an information providing API through the API calling unit in order to provide the measurement information on the user's biometric signal stored in the measurement information storage to the counselor's terminal or the user's terminal.

4. The remote medical service providing apparatus of claim 2, wherein when receiving a request for receiving the measurement information on the user's biometric signal from the user's terminal, the measurement information manager extracts the measurement information on the user's biometric signal from the measurement information storage and provides the measurement information on the user's biometric signal to the user's terminal.

5. The remote medical service providing apparatus of claim 1, wherein the service provider comprises a counselor connector to call, when receiving a request for receiving a remote medical service from the counselor's terminal, the call setup API through the API calling unit to try to establish a video telephony call setup between the counselor's terminal and the user's terminal.

6. The remote medical service providing apparatus of claim 5, wherein when the measurement information on the user's biometric signal received from the user's terminal is not within a predetermined normal range, the counselor connector automatically transmits information about the user to the counselor's terminal.

7. The remote medical service providing apparatus of claim 1, wherein when receiving a request for receiving exercise media from the counselor's terminal, the service provider calls a media API through the API calling unit in order to provide the received exercise media to the counselor's terminal or the user's terminal.

8. The remote medical service providing apparatus of claim 7, wherein when other exercise VoD content is additionally selected, the media enabler transmits information on a location at which the additionally requested exercise VoD content is stored to both the counselor's terminal and user's terminal, so that the counselor's terminal and user's terminal simultaneously display the additionally requested exercise VoD content.

9. The remote medical service providing apparatus of claim 1, wherein the API calling unit calls a corresponding API of an application gate, provided by the Open IPTV platform, according to a service type activated by a service provider.

10. An Open Internet Protocol Television (IPTV) platform apparatus comprising:
    an application gateway, provided by a processor, to provide a call setup application programming interface (API) an information providing API, and a media API of the IPTV platform for providing remote medical services; and
    an enabler to perform a function for providing the remote medical service according to a request from the APIs,
    wherein the remote medical service is provided via video telephony when the call setup API is called, and
    wherein each of the call setup API, the information providing API, and the media API corresponds to a different application service than the other APIs.

11. The Open IPTV platform apparatus of claim 10, further comprising a video telephony call setup API to try to establish a call setup between terminals,
    wherein the enabler comprises a call setup enabler to try to establish the call setup between the terminals using the call setup API.

12. The Open IPTV platform apparatus of claim 11, wherein the application gateway comprises an information providing API to provide measurement information on a user's biometric signal to at least one terminal,
    wherein the enabler comprises an information providing enabler to provide the measurement information on the user's biometric signal to the at least one terminal using the information providing API.

13. The Open IPTV platform apparatus of claim 10, further comprising a media API to provide media content to at least one terminal, wherein the enabler comprises a media enabler to provide information on a location at which exercise media content is stored, to at least one terminal, through the media API, according to a request for receiving the exercise media content.

14. A remote medical service providing method comprising:
- calling, when receiving a request for receiving a remote medical service from a counselor's terminal, a call setup API, an information providing API, and a media API of an Open Internet Protocol Television (IPTV) platform, such that the calling of the APIs is performed according to the request received from the counselor's terminal; and
- establishing a video telephony call setup between a user's terminal and a counselor's terminal using the call setup API, when the call setup API is called,
- wherein each of the call setup API, the information providing API, and the media API corresponds to a different application service than the other APIs.

15. The remote medical service providing method of claim 14, further comprising:
- receiving measurement data on a user's biometric signal from the user's terminal;
- databasing and storing the received measurement data on the user's biometric signal;
- comparing the received measurement data with a pre-stored reference value; and
- analyzing a result of the comparing.

16. The remote medical service providing method of claim 15, further comprising:
- extracting, when receiving a request for receiving information from the counselor's terminal, the measurement data on the user's biometric signal from stored measurement data on biometric signals;
- calling an information providing API; and
- providing the measurement data on the user's biometric signal to both the user's terminal and the counselor's terminal using the information providing API.

17. The remote medical service providing method of claim 14, further comprising:
- calling a media API according to a request for receiving exercise media content;
- detecting, a location at which the exercise media content is stored, using the media API; and
- transmitting the location at which the exercise media content is stored to both the user's terminal and the counselor's terminal using the media API.

* * * * *